US008879052B2

(12) United States Patent
Horowitz et al.

(10) Patent No.: US 8,879,052 B2
(45) Date of Patent: Nov. 4, 2014

(54) FLOATING-ELEMENT SHEAR-STRESS SENSOR

(75) Inventors: Stephen Brian Horowitz, Toney, AL (US); Mark Sheplak, Gainesville, FL (US); Toshikazu Nishida, Gainesville, FL (US); Louis Nicholas Cattafesta, III, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 205 days.

(21) Appl. No.: 12/936,832

(22) PCT Filed: Jun. 19, 2009

(86) PCT No.: PCT/US2009/047927
§ 371 (c)(1),
(2), (4) Date: Oct. 7, 2010

(87) PCT Pub. No.: WO2009/155499
PCT Pub. Date: Dec. 23, 2009

(65) Prior Publication Data
US 2011/0032512 A1    Feb. 10, 2011

Related U.S. Application Data

(60) Provisional application No. 61/074,030, filed on Jun. 19, 2008.

(51) Int. Cl.
*G01L 1/24* (2006.01)
*G02B 1/02* (2006.01)
*G01N 13/02* (2006.01)
*G02B 27/60* (2006.01)

(52) U.S. Cl.
CPC *G01N 13/02* (2013.01); *G02B 1/02* (2013.01); *G01N 2013/0216* (2013.01); *G02B 27/60* (2013.01)
USPC ........................................................ 356/35.5

(58) Field of Classification Search
CPC . G01N 13/02; G01N 2013/0216; G02B 27/60
USPC ................................................... 356/35.5, 73
See application file for complete search history.

(56) References Cited

U.S. PATENT DOCUMENTS 3,058,813 A * 10/1962 Barney, II et al. ........... 73/19.01
3,250,322 A *  5/1966 McCrary, Jr. et al. ........ 165/133
3,989,938 A * 11/1976 Auth .............................. 702/24

(Continued)

OTHER PUBLICATIONS

Gmitro et al., Confocal microscopy through a fiber-optic imaging bundle, Apr. 15, 1993, Optics Letters, vol. 18, No. 8, pp. 565-567.*

(Continued)

*Primary Examiner* — Michael A Lyons
*Assistant Examiner* — Shawn Decenzo
(74) *Attorney, Agent, or Firm* — Saliwanchik, Lloyd & Eisenschenk

(57) ABSTRACT

A shear-stress sensing system can include a floating element whose displacement can be detected through use of optical measurements. The system can utilize high temperature materials to deliver the optical signal to the structure to be measured, which can also utilize high temperature materials. In one embodiment, an intensity modulation or phase modulation of a reflected signal can be measured to determine the shear stress. In another embodiment, a Moire fringe pattern can be used to determine the shear stress.

18 Claims, 2 Drawing Sheets

(56) References Cited

U.S. PATENT DOCUMENTS

| | | |
|---|---|---|
| 4,641,027 A | 2/1987 | Renner |
| 5,052,228 A | 10/1991 | Haritonidis |
| 5,693,889 A | 12/1997 | Nadolink |
| 5,862,285 A * | 1/1999 | Danielian et al. .............. 385/121 |
| 5,870,511 A * | 2/1999 | Sawatari et al. ................. 385/12 |
| 7,262,912 B2 * | 8/2007 | Wood ............................. 359/459 |
| 2003/0081196 A1 | 5/2003 | Geiler |
| 2004/0129867 A1 | 7/2004 | Mackey |
| 2006/0079001 A1 | 4/2006 | Haidekker |
| 2006/0124870 A1 * | 6/2006 | Bobanovic et al. ......... 250/493.1 |
| 2006/0137467 A1 * | 6/2006 | Horowitz et al. ............... 73/815 |
| 2007/0258674 A1 | 11/2007 | Wang |

OTHER PUBLICATIONS

Kourouma, Named Youssouf Serge, "Design and Analysis of an Optical Detection Scheme for Micromachined Floating-Element Sear Stress Sensors," Master of Science Thesis, University of Florida, 2002.

\* cited by examiner

FLOATING-ELEMENT SHEAR-STRESS SENSOR

CROSS-REFERENCE TO RELATED APPLICATIONS

This application is the U.S. national stage application of International Patent Application No. PCT/US2009/047927, filed Jun. 19, 2009, which claims priority to U.S. Provisional Patent Application No. 61/074,030, filed Jun. 19, 2008, the disclosures of each of which are incorporated herein by reference in their entirety.

FIELD OF THE INVENTION

The invention relates to sensors, and more particularly to shear-stress sensors.

BACKGROUND

The measurement of mean and fluctuating wall shear-stress in laminar, transitional, and turbulent boundary layers and channel flows has applications both in industry and the scientific community. Time-resolved, fluctuating shear-stress data can also provide physical insight into complex flow phenomena, including turbulent viscous drag, transition to turbulence, flow separation, and shock-wave/boundary layer interactions. For example, the accurate measurement of skin friction is important to the aircraft industry.

Unfortunately, macro-scale measurement technology is insufficient to meet the demands of directly obtaining accurate mean and fluctuating wall shear stress data. More specifically, the accurate, direct measurement of fluctuating wall shear stress has not been realized via conventional measurement technology.

Micromachining technology provides the opportunity to synthesize transducers possessing superior performance compared to mainstream mechanical fabrication techniques. Specifically, the small physical size and corresponding reduced mass of micro-sensors offers the potential to vastly improve both the temporal and spatial measurement bandwidth.

Realizing the potential advantages of miniaturization scaling, the MEMS community has developed both thermal, floating element, and optical shear-stress sensors. Thermal sensors are generally robust and simpler to fabricate. However, they are based on a heat transfer analogy and absolute calibration for quantitative measurements is difficult. Optical MEMS (MOEMS)-based laser-Doppler anemometers that measure velocity gradients in the viscous sublayer are also known, but the ability to generate a sufficiently small measurement volume in a high-Reynolds number sublayer is challenging.

Floating-element structures provide a good opportunity to obtain direct quantitative, time-resolved measurements in a controlled wind tunnel environment. Several transduction techniques are known for measurement of the shear-stress induced deflection of floating elements, including capacitive, piezoresistive, and differential optical shutter techniques. However, such techniques have limitations, including thermal management issues, lacking the ability to be flush-mountable with no wire bonds that generate flow disturbances, and being subject to electromagnetic interference and pressure fluctuations.

SUMMARY OF THE INVENTION

In one exemplary embodiment, a shear-stress sensor system can include a floating element operably connected to a structure and displaceable with respect to the structure based on a shear stress induced in the structure; a light source for generating an optical signal; a first optical fiber in proximity to the floating element and positioned non-orthogonal to the floating element where the first optical fiber is operably connected to the light source for delivery of the optical signal to the floating element; and a second optical fiber in proximity to the floating element and positioned non-orthogonal to the floating element. The second optical fiber can receive a reflected signal based on the optical signal. The reflected signal can be intensity modulated and proportional to a deflection of the floating element.

In another exemplary embodiment, a shear-stress sensor system can include a floating element operably connected to a structure and displaceable with respect to the structure based on a shear stress induced in the structure; a light source for generating an optical signal; and an optical fiber in proximity to the floating element and positioned orthogonal to the floating element. The optical fiber can be operably connected to the light source for delivery of the optical signal to the floating element. The optical fiber can receive a reflected signal based on the optical signal. The reflected signal can be intensity modulated based on a spreading of the optical signal in free space after exiting the optical fiber. The intensity modulation of the reflected signal can be proportional to a deflection of the floating element.

In another exemplary embodiment, a shear-stress sensor system can include a floating element operably connected to a structure and displaceable with respect to the structure based on a shear stress induced in the structure; a light source for generating an optical signal; an optical fiber in proximity to the floating element and being operably connected to the light source for delivery of the optical signal to the floating element where the optical fiber is a single mode fiber capable of coherent transmission of light; and an interferometer operably connected to the optical fiber. The optical fiber can receive a reflected signal based on the optical signal, where the reflected signal is phase modulated and delivered to the interferometer, and where the phase modulation of the reflected signal is proportional to a deflection of the floating element.

In another exemplary embodiment, a system for determining a shear stress in a structure can include a substrate support connected to the structure and having a first optical grating with a plurality of features defining a first spatial period; a floating element having a second optical grating with a plurality of features defining a second spatial period where the floating element is suspended over the first optical grating and flexibly connected to the substrate with compliant springs and where the first and second gratings are in an optical path with one another and form a Moiré fringe pattern when illuminated, which relates to a shear-stress induced translation of the floating element; an imaging device; and an optical fiber bundle operably connected to the structure and having a distal end in proximity to the floating element for detecting and delivering the Moiré fringe pattern to the imaging device.

BRIEF DESCRIPTION OF THE DRAWINGS

There is shown in the drawings embodiments which are presently preferred, it being understood, however, that the invention can be embodied in other forms without departing from the spirit or essential attributes thereof.

DETAILED DESCRIPTION OF THE INVENTION

The exemplary embodiments disclosed herein can utilize a floating-element shear stress sensor that permits direct, high-temperature measurement of skin friction based on geometric and/or interferometric optical techniques. The exemplary embodiments describe a number of systems and methods or techniques that can directly modulate an optical signal in response to a displacement. These techniques can be implemented as described herein for the measurement of a shear-stress induced, floating element deflection using high temperature, thermally matched materials. Geometrical optical techniques that are directly applicable to this approach can include optical lever and Moiré grating methods, while interferometric techniques can be implemented in configurations such as a Mach-Zender, Fabry-Perot, or Michelson type interferometer configuration. Using one or more of these optical transduction techniques, the extension of shear stress measurement to higher temperatures can be enabled by the availability of high-temperature materials that can transmit, absorb and/or reflect optical signals.

Figure 1:
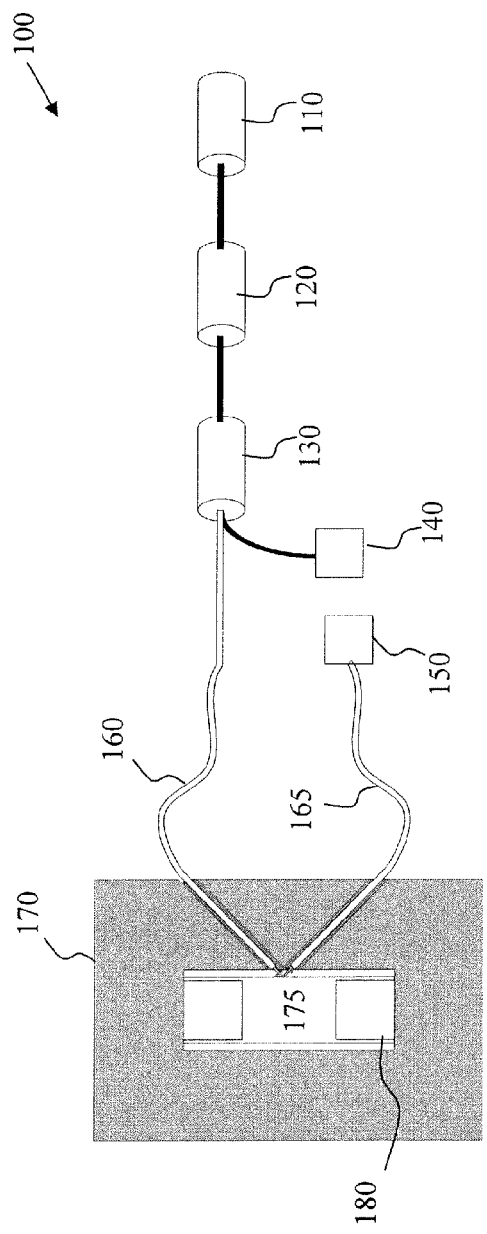
FIG. 1 illustrates a system of determining shear stress according to an exemplary embodiment of the present invention.

Referring to FIG. 1, a sensing system is shown and generally represented by reference numeral 100. System 100 can be operable for determining shear stress associated with a conduit or other structure. System 100 can include a laser or other optical source 110 for generating an optical signal or beam to be transmitted through an optical isolator 120 and a coupler 130, and delivered to a floating element sensor 175 via a first optical fiber 160. The first optical fiber 160 can be a high temperature optical fiber, such as made from sapphire. A photo-detector 140 can be operably coupled to the coupler 130 for data acquisition of the optical signal being delivered to the floating element 175. Under an applied shear stress, the floating element 175 can deflect (e.g., laterally) due to the use of compliant tethers 180 attached to a substrate 170.

The first optical fiber 160 can be positioned at an angle to a vertical plane of the floating element 175 (e.g., at a non-orthogonal angle to a sidewall of the floating element 175). A second optical fiber 165, preferably of the same material as the first optical fiber 160, can be positioned at an angle to the vertical plane of the floating element 175 and can receive the optical signal which has been reflected off of the floating element 175 or some other structure connected thereto.

The reflected signal can be delivered to a second photo-detector 150 operably coupled to the second optical fiber 165. The angles for the first and second optical fibers 160, 165 can be equal but opposite to each other to allow for the optical signal to be reflected and received by the second optical fiber. The particular angles utilized can vary and can depend on a number of factors, such as the shape and structure of the conduit or structure that is being monitored. The distal ends of the first and second optical fibers 160, 165 can be positioned hi proximity to the floating element 175 and can be routed thereto in a number of ways, including openings formed through the sidewall of the substrate 170 or the conduit (or structure).

Shear-stress induced deflection of the floating element 175 can result in a transverse displacement of the reflected optical signal. The second optical fiber 165 can return an intensity modulated signal to the photo-detector 150 where the signal is proportional to the floating element deflection and which results from the proportional misalignment between the displaced free space beam and the second optical fiber 165. The present disclosure contemplates the vertical plane of the floating element 175 being a physical sidewall of the floating element or another structure that is associated with the floating element that undergoes proportional shear stress displacement, such as a secondary vertical structure that is directly attached to the floating element and undergoes the same shear-stress induced deflection.

Figure 2:
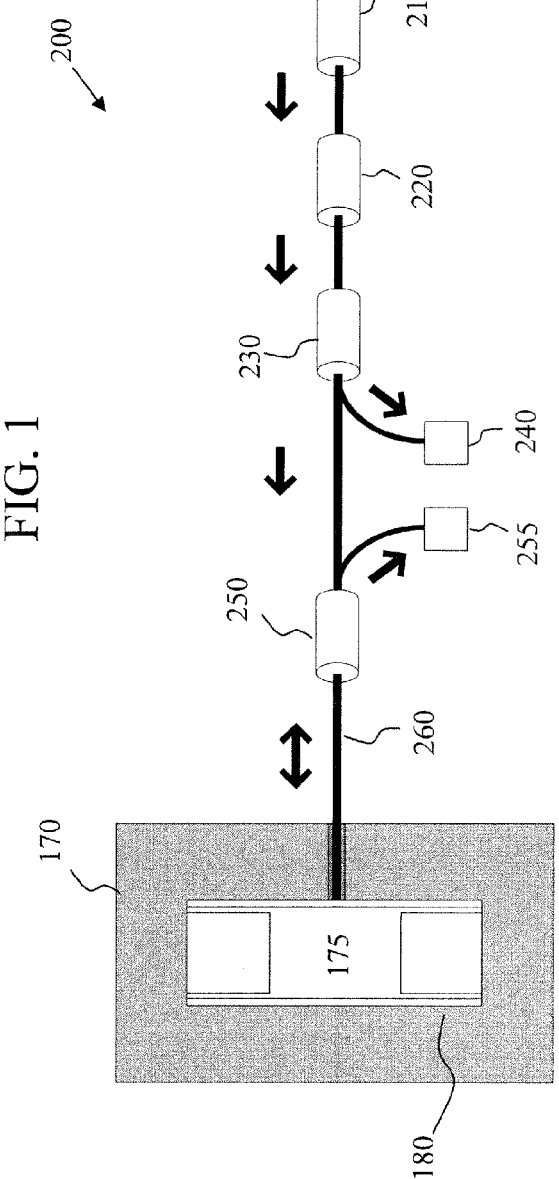
FIG. 2 illustrates a system of determining shear stress according to another exemplary embodiment of the present invention.

Referring to FIG. 2, a sensing system is shown and generally represented by reference numeral 200. System 200 can be operable for determining shear stress associated with the conduit or other structure. System 200 can include a laser or other optical source 210 for generating an optical signal or beam to be transmitted through an optical isolator 220, a first coupler 230, and a second coupler 250, and delivered to the floating element sensor 175 via an optical fiber 260. The optical fiber 260 can be a high temperature optical fiber, such as made from sapphire. Photo-detectors 240 and 255 can be operably coupled to couplers 230 and 250, respectively, for data acquisition of the optical signal being delivered to, and reflected from, the floating element 175. As described above, under an applied shear stress, the floating element 175 can deflect (e.g., laterally) due to the use of the compliant tethers 180 attached to the substrate 170.

The optical fiber 260 can be positioned normal to, or orthogonal with, a vertical plane of the floating element 175 (e.g., perpendicular to a sidewall of the floating element 175). The optical fiber 260 can be utilized for both delivery of the optical signal to the floating element 175 and receipt of the reflected signal from the floating element 175. The distal end of the optical fiber 260 can be positioned in proximity to the floating element 175 and can be routed thereto in a number of ways, including an opening formed through the sidewall of the substrate 170 or the conduit (or structure).

Shear-stress induced deflection of the floating element 175 can result in a transverse displacement of the reflected optical signal. In this instance, the spreading of the free-space beam after exiting the fiber 260 can result in a modulated intensity that is proportional to the floating element deflection. The optical fiber 260 can return the modulated signal to the photo-detector 255, the modulated signal being proportional to the floating element deflection.

Figure 3:
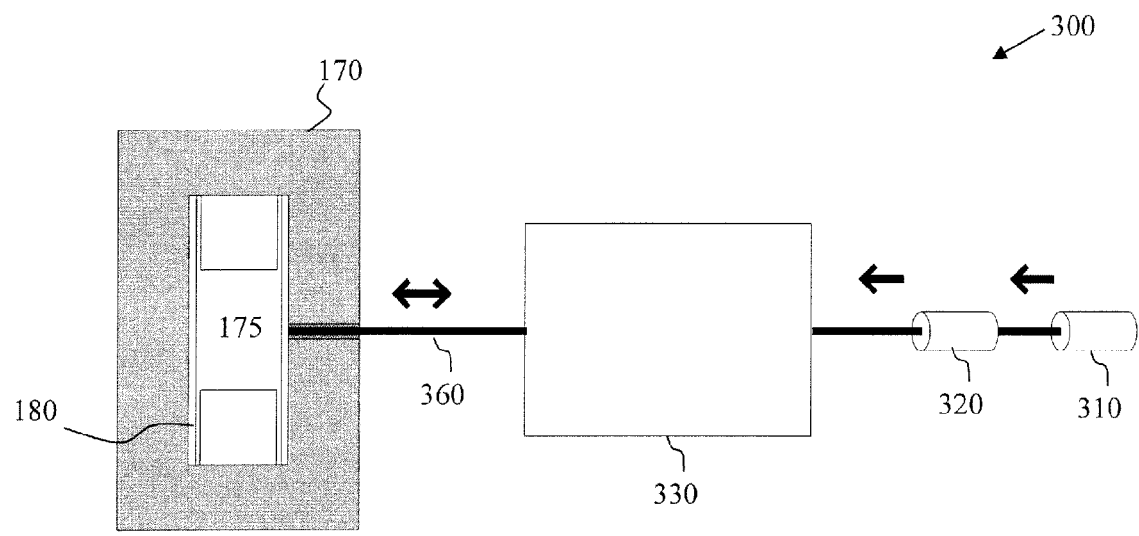
FIG. 3 illustrates a system of determining shear stress according to another exemplary embodiment of the present invention.

Referring to FIG. 3, a sensing system is shown and generally represented by reference numeral 300. System 300 can be operable for determining shear stress associated with the conduit or other structure. System 300 can include a laser or other optical source 310 for generating an optical signal or beam to be transmitted through an optical isolator 320 and an interferometer 330, and delivered to the floating element sensor 175 via an optical fiber 360. The optical fiber 360 can be a high temperature optical fiber, such as made from sapphire. As described above, under an applied shear stress, the floating element 175 can deflect (e.g., laterally) due to the use of the compliant tethers 180 attached to the substrate 170.

The optical fiber 360 can be positioned normal to, or orthogonal with, a vertical plane of the floating element 175 (e.g., perpendicular to a sidewall of the floating element 175). The optical fiber 360 can be utilized for both delivery of the optical signal to the floating element 175 and receipt of the reflected signal from the floating element. The distal end of the optical fiber 360 can be positioned in proximity to the floating element 175 and can be routed thereto in a number of ways, including an opening formed through the sidewall of the substrate 170 or the conduit (or structure).

The optical fiber 360 can be a single-mode fiber, capable of coherent transmission of light, thereby enabling interferometric modulation of the optical signal. The optical signal or beam reflected by the vertical plane of the floating element 175 can be phase modulated due to the shear stress and resulting displacement of the floating element, such that the phase is proportional to the shear stress induced deflection. By maintaining coherence, the phase modulated optical signal or beam can be recombined with an unmodulated optical reference signal to produce an intensity variation in the returned optical signal.

Depending upon the source of the reference signal, various interferometer configurations can be utilized by system 300. In one embodiment, the partial reflection from the fiber end face can be used as a reference in order to establish a Fabry-Perot configuration. In another embodiment, the optical signal can be split into two parts prior to the fiber end face in order to establish a Michelson or Mach-Zender configuration, depending upon the waveguide topology that is utilized.

Figure 4:
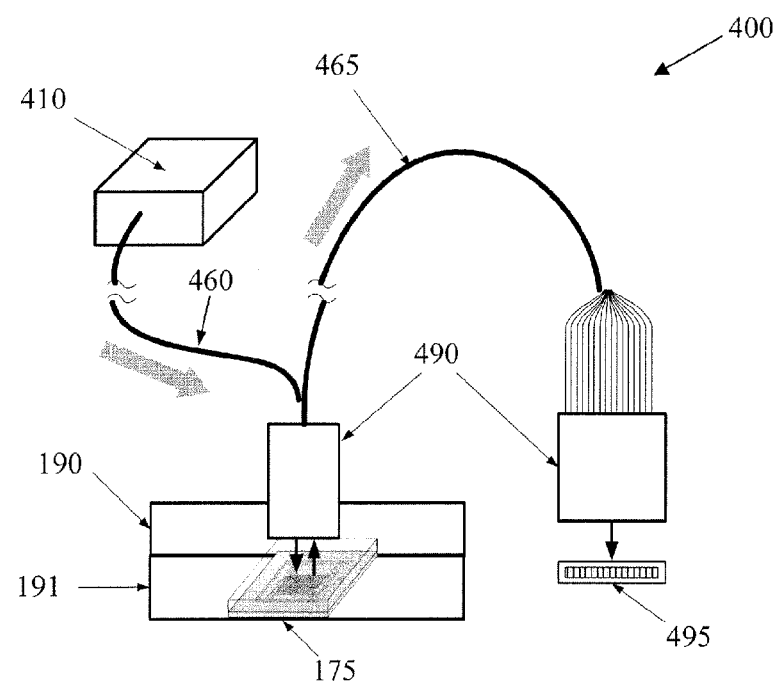
FIG. 4 illustrates a system of determining shear stress according to another exemplary embodiment of the present invention.

Referring to FIG. 4, a sensing system is shown and generally represented by reference numeral 400. System 400 can be operable for determining shear stress associated with the conduit or other structure. System 400 can employ the principle of geometric Moiré transduction through generation of an optical signal or beam by the light source 410 which is delivered to the floating element 175 via the fiber 460.

A Moiré fringe pattern can occur when two gratings of almost identical spatial period are superimposed, and can be regarded as a type of spatial beating phenomenon. For shear stress sensing, the Moiré pattern can be produced by patterning one grating on a fixed base structure 190 and a second grating on the movable floating element 175 directly above the base grating. The floating element can be connected to the base structure 190 via compliant tethers or springs (e.g., tethers 180).

One example of a structure and configuration of the floating element 175 that can be used in this exemplary embodiment is described in U.S. Patent Application Publication No. 2006/0137467 to Horowitz et al., the disclosure of which is hereby incorporated by reference. Gratings can be defined within the substrate and/or floating element using a variety of processes to define first and second grating patterns. The floating element 175 can be in an optical path of the system 400, such as being suspended over the first grating and flexibly connected to the substrate with compliant tethers or springs so that the first and second gratings overlay one another.

When the device is illuminated, light can be reflected by the superimposed top and bottom gratings, creating the translation-dependent Moiré fringe pattern. Under an applied shear stress, the floating element can deflect due to the compliant tethers, resulting in a displacement of one grating with respect to the other. This leads to a correspondingly larger displacement of the Moiré pattern. The Moiré fringe shift can amplify small displacements by the ratio of the fringe pitch to the movable grating pitch. This ratio can be made sufficiently large enough to amplify the floating element displacement by several orders of magnitude, thereby facilitating measurement of the applied shear stress.

For high temperature operation, the gratings can be constructed of a high melting, high eutectic point material, such as platinum, while the floating element can be constructed of a high temperature material of lower reflectance, such as silicon carbide. The bottom gratings can be supported by an optically transparent base (e.g., base structure 190) constructed of a high temperature, transparent material, such as sapphire. A steel or sapphire housing (191) can be included.

The Moiré fringe pattern can be routed off-sensor via an optical fiber bundle 465 and packaging 490, and detected using an imaging system (e.g., a digital imaging system), such as a CCD camera, CMOS camera, discrete photodectors or photodiode array 495. The phase of the Moiré pattern can then be determined from the recorded image. This technique can provide for immunity to electromagnetic interference and intensity fluctuations of the light source 410, as only the phase of the Moiré pattern needs to be evaluated. The optical fiber bundle 465 can be a sapphire optical bundle. Furthermore, the sapphire bundle is capable of high temperature operation allowing for remote and protected placement of the more temperature sensitive electronics of the system.

The optical shear stress sensing systems can include various features such as use of high temperature materials coupled with optical transduction of a shear-stress induced floating element deflection to enable high temperature shear stress measurements; use of two angled, in-plane optical fibers for floating element deflection using optical leverage resulting from beam displacement; use of a single, multi-mode, normal-incidence, in-plane optical fiber for floating deflection using optical leverage resulting from beam spreading; use of high-temperature materials, such as sapphire, for the optical lever fibers and transparent sensor base; use of high-temperature materials, such as silicon carbide, for the floating element; use of matched thermal coefficients of expansion (TCE) of the sensor materials for reduced temperature induced stress; use of a single-mode, high-temperature optical fiber for floating deflection using interferometric techniques, such as Michelson, Mach-Zender, and Fabry-Perot; detection of Moiré fringe patterns using high-temperature, optical fiber bundles and a digital imaging system; use of high temperature (e.g., platinum) periodic grating structure on a high-temperature (e.g., silicon carbide) floating element sensor; use of a high-temperature transparent base (e.g., sapphire) that provides backside optical access to the sensor; and/or enabling flush mounting of the sensor front side.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A system for determining shear stress in structures, the system comprising:
a substrate support connected to a structure and having a first optical grating with a plurality of features defining a first spatial period;
a floating element having a second optical grating with a plurality of features defining a second spatial period, the floating element being suspended over the first optical grating and flexibly connected to the substrate with compliant tethers or springs, wherein the first and second gratings are in an optical path with one another and form a Moiré fringe pattern when illuminated that relates to a shear-stress induced translation of the floating element;
an imaging device; and an optical fiber bundle operably connected to the structure and having a distal end in proximity to the floating element for detecting and delivering the Moiré fringe pattern to the imaging device,
wherein in a delivery path of a signal reflected from the floating element, the system consists of the optical fiber bundle between the floating element and the imaging device.

2. The system of claim 1, wherein the optical fiber bundle comprises sapphire.

3. The system of claim 1, wherein the substrate support and the floating element are part of a micro-electrical-mechanical system (MEMS) shear-stress sensor, wherein the substrate support comprises sapphire.

4. The system of claim 1, wherein the first and second optical gratings comprise platinum.

5. The system of claim 1, wherein the floating element comprises silicon carbide.

6. The system of claim 1, wherein the imaging device comprises a photodiode array.

7. The system of claim 1, wherein the imaging device comprises a plurality of discrete photodetectors.

8. The system of claim 1, wherein the imaging device comprises a CCD camera.

9. The system of claim 1, wherein the imaging device comprises a CMOS camera.

10. The system of claim 1, wherein the floating element comprises sapphire.

11. The system of claim 1, wherein the optical fiber bundle comprises a high temperature material.

12. The system of claim 1, wherein the floating element comprises a high temperature material.

13. The system of claim 1, wherein the substrate support comprises an optically transparent, high temperature material.

14. The system of claim 1, wherein the first and second optical gratings comprise an optically reflective, high temperature material.

15. The system of claim 1, wherein the first and second optical gratings comprise an optically absorbing material and the floating element comprises an optically reflective material.

16. The system of claim 1, further comprising a second optical fiber bundle having a distal end in proximity to the floating element for delivering an optical signal to the floating element.

17. The system of claim 16, wherein the distal end of the optical fiber bundle for detecting and delivering the Moiré fringe pattern to the imaging device and the distal end of the second optical fiber bundle for delivering the optical signal to the floating element are provided in a package disposed proximate the floating element.

18. The system of claim 15, wherein the first and second optical gratings comprise high temperature materials.

* * * * *